United States Patent [19]

Okawa

[11] Patent Number: 5,847,178
[45] Date of Patent: Dec. 8, 1998

[54] METHOD FOR PURIFYING 3-METHACRYLOXY-PROPYLDIMETHYLHALOSILANES AND 3-METHACRYLOXYPROPYL-METHYLDIHALOSILANES

[75] Inventor: Tadashi Okawa, Chiba Prefecture, Japan

[73] Assignee: Dow Corning Toray Silicone Co., Ltd., Tokyo, Japan

[21] Appl. No.: 982,768

[22] Filed: Dec. 2, 1997

[30] Foreign Application Priority Data

Dec. 2, 1996 [JP] Japan .................................. 8-336332

[51] Int. Cl.$^6$ ....................................................... C07F 7/08
[52] U.S. Cl. .................................................. 556/440
[58] Field of Search ............................................. 556/440

[56] References Cited

U.S. PATENT DOCUMENTS 5,262,555  11/1993  Okawa et al. ........................... 556/440

FOREIGN PATENT DOCUMENTS 7-316164  of 1995  Japan .

OTHER PUBLICATIONS

Cameron et al., "Polymerization of poly(dimethylsiloxane)macromers: 1. Copolymerization. . .".
English abstract of Hei 7–316164, 1995.

*Primary Examiner*—Paul F. Shaver
*Attorney, Agent, or Firm*—William F. Boley; Jennifer S. Warren

[57] ABSTRACT

A method for purifying 3-methacryloxypropyldimethylhalosilanes or 3-methacryloxypropyl methyldihalosilanes which is characterized by the fact that 1-methyl-2-methacryloxyethyldimethyl halosilanes or 1-methyl-2-methacryloxyethylmethyldihalosilanes contained in products or fractions consisting of 3-methacryloxypropyldimethylhalosilanes or 3-methacryloxypropylmethyl dihalosilanes produced by a hydrosilation reaction of allyl methacrylate with dimethylhalosilanes or methyldihalosilanes are decomposed by means of at least one copper compound selected from the group consisting of copper hydroxides, copper salts other than copper halides, and copper oxides, after which these compounds are subjected to fractional distillation.

14 Claims, No Drawings

METHOD FOR PURIFYING 3-METHACRYLOXY-PROPYLDIMETHYLHALOSILANES AND 3-METHACRYLOXYPROPYL-METHYLDIHALOSILANES

BACKGROUND OF INVENTION

The present invention is a method for purifying 3-methacryloxypropyldimethylhalosilanes and 3-methacryloxypropylmethyldihalosilanes. More specifically, the present invention is a method in which 1-methyl-2-methacryloxyethyldimethylhalosilanes or 1-methyl-2-methacryloxyethylmethyldihalosilanes contained in products or fractions consisting of 3-methacryloxypropyldimethylhalosilanes or 3-methacryloxypropylmethyldihalosilans produced by a hydrosilation reaction of allyl methacrylate with dimethyl halosilanes or methyldihalosilanes are decomposed, thus facilitating the fractional distillation of these compounds so that 3-methacryloxypropyldimethylhalosilanes or 3-methacryloxypropylmethyldihalosilanes can be purified to a high purity.

A method in which 3-methacryloxypropyldimethylhalosilanes or 3-methacryloxypropyl methyldihalosilanes are manufactured by subjecting allyl methacrylate and dimethylhalosilanes or methyldihalosilanes to a hydrosilation reaction, and then subjecting the resulting products to a fractional distillation is known (Polymer 26: 437, 1985). When these products are subjected to a fractional distillation, a polymerization blocking agent is generally added in order to prevent gelation of the 3-methacryloxypropyldimethylhalosilanes or 3-methacryloxypropylmethyldihalosilanes. It is also known that 3-methacryloxypropyldimethyl halosilanes or 3-methacryloxypropylmethyldihalosilanes can be fractionated with a good yield by using copper (II) oxide or copper sulfates as such polymerization blocking agents (see Japanese Patent Application Kokai No. 7-316164). However, even using fractional distillation, it has not been possible to purify 3-methacryloxypropyldimethylhalosilanes or 3methacryloxypropylmethyl dihalosilanes to a high purity. In investigating the causes of this, the present inventors found that products consisting of 3-methacryloxypropyldimethylhalosilanes or 3-methacryloxypropylmethyl dihalosilanes produced by a hydrosilation reaction of allyl methacrylate with dimethylhalosilanes or methyldihalosilanes, as well as fractions obtained by subjecting such products to a fractional distillation, contain small amounts of 1-methyl-2-methacryloxyethyldimethylhalosilanes or 1- methyl-2-methacryloxyethylmethyldihalosilanes which are by-products of the hydrosilation reaction. The boiling points of these 1-methyl-2-methacryloxyethyldimethylhalosilanes or 1-methyl-2-methacryloxyethylmethyldihalosilanes are close to the boiling points of 3-methacryloxypropyldimethylhalosilanes or 3methacryloxypropylmethyldihalosilanes, so that it is difficult to separate these compounds. Accordingly, the purity of the 3methacryloxypropyl dimethylhalosilanes or 3methacryloxypropylmethyldihalosilanes drops. Such 1-methyl-2-methacryloxyethyldimethylhalosilanes or 1-methyl-2-methacryloxyethylmethyldihalosilanes contained in 3-methacryloxypropyldimethylhalosilanes or 3-methacryloxypropyl methyldihalosilanes sometimes create problems. For example, 1-methyl-2methacryloxyethyl dimethylchlorosilane produces impurities such as dimethyldichlorosilane by the following decomposition and interchange reactions:

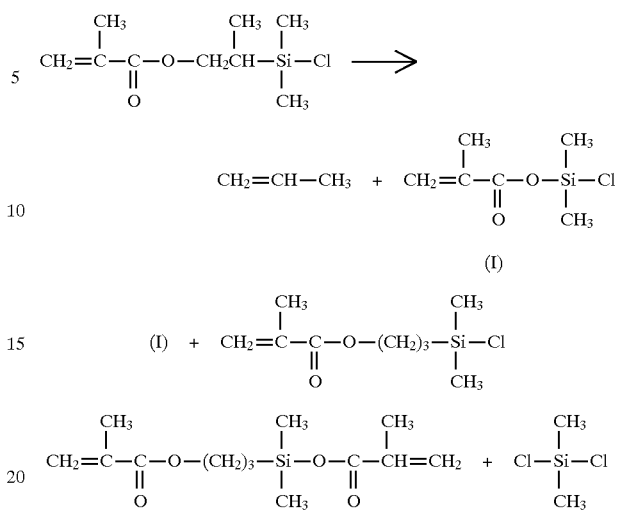

(Formula 1)

In investigating copper (II) oxide and copper sulfates as polymerization blocking agents for use in the abovementioned fractional distillation, the present inventors discovered that 1-methyl-2-methacryloxyethyldimethylhalosilanes or 1-methyl-2-methacryloxyethylmethyldihalosilanes contained in products consisting of 3-methacryloxypropyldimethylhalosilanes or 3-methacryloxypropylmethyldihalosilanes or selectively decomposed, and that by thoroughly decomposing these silanes, and then subjecting these compounds to a fractional distillation, it is possible to purify 3-methacryloxypropyldimethylhalosilanes or 3-methacryloxypropylmethyl dihalosilanes to a high degree of purity. This discovery led to the perfection of the present invention. Furthermore, the inventors also discovered that in addition to copper (II) oxide and copper sulfates, other copper compounds such as copper hydroxides, copper salts other than copper halides, and copper oxides also promote the abovementioned decomposition reaction.

Specifically, the object of the present invention is to provide a method in which 1-methyl-2-methacryloxyethyldimethylhalosilanes or 1-methyl-2-methacryloxyethylmethyldihalosilanes contained in products or fractions consisting of 3-methacryloxypropyldimethylhalosilanes or 3-methacryloxypropylmethyldihalosilanes produced by a hydrosilation reaction of allyl methacrylate with dimethylhalosilanes or methyldihalosilanes are decomposed, thus facilitating the fractional distillation of these compounds so that 3-methacryloxypropyldimethylhalosilanes or 3-methacryloxypropylmethyldihalosilanes can be purified to a high purity.

SUMMARY OF INVENTION

The present invention is a method for purifying 3-methacryloxypropyldimethylhalosilanes or 3-methacryloxypropylmethyldihalosilanes which is characterized by the fact that 1-methyl-2-methacryloxyethyldimethylhalosilanes or 1-methyl-2-methacryloxyethylmethyldihalosilanes contained in products or fractions consisting of 3-methacryloxypropyldimethylhalosilanes or 3-methacryloxypropylmethyldihalosilanes produced by a hydrosilation reaction of allyl methacrylate with dimethylhalosilanes or methyldihalosilanes are decomposed by means of at least one copper compound selected from the group consisting of copper hydroxides, copper salts other than copper halides, and copper oxides, after which these compounds are subjected to a fractional distillation.

DESCRIPTION OF INVENTION

The present invention is a method for purifying 3-methacryloxypropyldimethylhalosilanes or 3-methacryloxypropylmethyldihalosilanes characterized by the fact that 1-methyl-2-methacryloxyethyldimethylhalosilanes 1-methyl-2-methacryloxyethylmethyldihalosilanes contained in products or fractions consisting of 3-methacryloxypropyldimethylhalosilanes or 3-methacryloxypropylmethyldihalosilanes produced by a hydrosilation reaction of allyl methacrylate with dimethylhalosilanes or methyldihalosilanes are decomposed by means of at least one copper compound selected from the group consisting of copper hydroxides, copper salts other than copper halides, and copper oxides, after which these compounds are subjected to a fractional distillation.

A product consisting of 3-methacryloxypropyldimethylhalosilanes or 3-methacryloxypropyl methyldihalosilanes produced by a hydrosilation reaction of allyl methacrylate with dimethylhalosilanes or methyldihalosilanes, or a fraction obtained by subjecting such a product to a fractional distillation, is used in the purification method of the present invention. Examples of such dimethylhalosilanes or methyldihalosilanes include dimethylfluorosilane, dimethylchlorosilane, dimethylbromosilane, dimethyliodosilane, methyldifluorosilane, methyldichlorosilane, methyldibromosilane, and methyldiiodosilane. Dimethylchlorosilane and methyldichlorosilane are especially desirable.

Examples of catalysts which promote this hydrosilation reaction include transition metal type catalysts such as platinum, palladium, rhodium, ruthenium, cobalt, and nickel. Especially desirable are platinum type catalysts such as chloroplatinic acid, alcohol solutions of chloroplatinic acid, ketone solutions of chloroplatinic acid, ether solutions of chloroplatinic acid, olefin complexes of platinum, alkenylsiloxane complexes of platinum, carbonyl complexes of platinum, platinum black, platinum supported on powdered silica, and platinum supported on powdered activated carbon.

The use of organic solvents is optional in the abovementioned hydrosilation reaction, and the addition of known polymerization blocking agents is also optional. Examples of such organic solvents include solvents which do not hinder the hydrosilation reaction, such as aromatic solvents such as toluene and xylene and aliphatic solvents such as hexane and heptane. Furthermore, examples of polymerization blocking agents which can be used include phenothiazine, hindered phenol compounds, amine compounds, quinone compounds, polyphenol derivatives, and oxygen.

Products consisting of 3-methacryloxypropyldimethylhalosilanes or 3-methacryloxypropyl methyldihalosilanes produced by a hydrosilation reaction of allyl methacrylate with dimethyl halosilanes or methyldihalosilanes, as well as fractions obtained by subjecting such products to a fractional distillation, contain small amounts of 1-methyl-2-methacryloxyethyldimethylhalosilanes or 1-methyl-2-methacryloxyethylmethyldihalosilanes which are by-products of the reaction. In the present method the 1-methyl-2-methacryloxyethyldimethylhalosilanes or 1-methyl-2-methacryloxyethylmethyldihalosilanes are selectively decomposed by means of at least one copper compound selected from the group consisting of copper salts other than copper halides, copper oxides, and copper hydroxides; thus facilitating the purification and separation of 3-methacryloxypropyldimethylhalosilanes or 3-methacryloxypropylmethyldihalosilanes.

The abovementioned copper compounds used in the present method is at least one copper compound selected from the group consisting of copper hydroxides, copper salts other than copper halides, and copper oxides. Examples of such copper hydroxides include copper (I) hydroxide and copper (II) hydroxide. Furthermore, examples of the abovementioned copper salts include compounds formed by copper (I) ions or copper (II) ions and conjugate bases of organic acids or inorganic acids; with specific examples of such compounds including copper (I) sulfate, copper (II) sulfate, copper (I) nitrate, copper (II) nitrate, copper (I) acetate and copper (II) acetate. In this case, copper sulfates such as copper (I) sulfate and copper (II) sulfate and copper acetates such as copper (I) acetate and copper (II) acetate, are desirable, and copper (II) sulfate and copper (II) acetate are especially desirable. Examples of the abovementioned copper oxides include copper (I) oxide and copper (II) oxide.

Examples of the compounds produced when 1-methyl-2-methacryloxyethyldimethyl halosilanes or 1-methyl-2-methacryloxyethylmethyldihalosilanes are decomposed by means of at least one copper compound selected from the group consisting of copper hydroxides, copper salts other than copper halides, and copper oxides, include methacryloxydimethylhalosilanes or methacryloxymethyldihalosilanes, propene and dimethyldihalosilanes or methyltrihalosilanes. The boiling points of these compounds are lower than the boiling points of 3-methacryloxypropyldimethylhalosilanes or 3-methacryloxypropylmethyldihalosilanes. Accordingly, by subjecting these compounds to a fractional distillation, it is possible to purify 3-methacryloxypropyldimethylhalosilanes or 3-methacryloxypropylmethyldihalosilanes to a high degree of purity.

There are no restrictions on the amounts of the abovementioned one or more copper compounds selected from the group consisting of copper hydroxides, copper salts other than copper halides, and copper oxides that are added; the amounts added depend on the conditions of the decomposition reaction of the 1-methyl-2-methacryloxyethyldimethylhalosilanes or 1-methyl-2-methacryloxyethylmethyldihalosilanes. Generally, however, it is desirable that the amount added be in the range of 0.01 to 20 parts by weight, preferably 0.1 to 10 parts by weight, per 100 parts by weight of the abovementioned 3-methacryloxypropyldimethylhalosilanes or 3-methacryloxypropyl methyldihalosilanes.

It is desirable that this decomposition reaction be performed without using a solvent; however, the reaction may also be performed in the presence of an organic solvent. Furthermore, although this decomposition reaction may also be performed at room temperature, it is desirable that the reaction be performed with the reaction system heated to a temperature of 50° to 200° C. When 3-methacryloxypropyldimethylhalosilanes or 3-methacryloxypropylmethyldihalosilanes are subjected to a fractional distillation following the completion of this decomposition reaction, a universally known polymerization blocking agent such as phenothiazine, a hindered phenol compound, an amine compound, a quinone compound, or oxygen may also be added in order to inhibit polymerization of the silanes.

Below, the present method for purifying 3-methacryloxypropyldimethylhalosilanes or 3-methacryloxypropylmethyldihalosilanes will be described in detail in terms of examples.

Comparative Example 1. 1000 g (7.94 moles) of Allyl methacrylate and 1 g of 3,5-di-tbutyl-4-hydroxyphenylmethyldimethylammoniunchloride were placed in a four-necked flask equipped with an agitator; furthermore, a 1,1,3,3-tetramethyl-1,3-divinyldisiloxane complex of platinum was added in an amount which was such that the weight ratio of platinum metal to allyl methacrylate was 20 ppm. This system was heated to 90° C. in a nitrogen atmosphere, and a small amount of dimethylchlorosilane was added dropwise. After the initiation of a hydrosilation reaction was confirmed, a total amount of 682 g (7.22 moles) of dimethylchlorosilane was added dropwise while the reaction temperature was maintained at 85° to 95° C. by subjecting this system to water cooling or air cooling. Following the completion of this dropwise addition, the system was agitated for 30 minutes at 80° C., thus producing a product consisting of 3-methacryloxypropyldimethylchlorosilane. This product was analyzed by gas chromatography using a capillary column and an FID detector (hereafter referred to as capillary GLC), and by $^{13}$C-nuclear magnetic resonance analysis. It was ascertained that this product contained approximately 2 mol % 1-methyl-2-methacryloxyethyldimethylchlorosilane.

Next, 1 g of 2,6-di-t-butyl-4-methylphenol was added to this product, and distillation was performed under reduced pressure at 5 mmHg, thus producing a fraction with a boiling point of 92° to 105° C. This fraction was subjected to $^{13}$C-nuclear magnetic resonance analysis and $^{29}$Si-nuclear magnetic resonance analysis. As a result, it was ascertained that this product consisted of 93.1% 3-methacryloxypropyldimethylchlorosilane described by formula

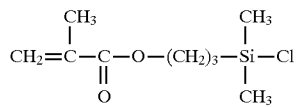

2.4% 1-methyl-2-methacryloxyethyldimethylchlorosilane described by the formula

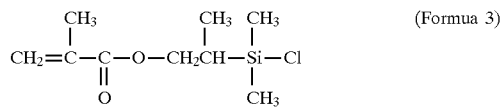

(Formua 3)

1.3% 3-methacryloxypropyl(methacryloxy)dimethylsilane described by the formula

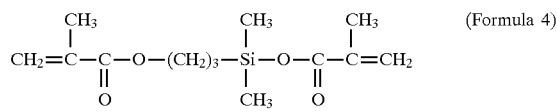

(Formula 4)

0.6% methacryloxydimethylchlorosilane described by the formula

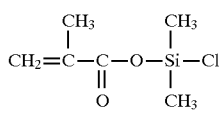

(Formula 5)

0.8% dimethyldichlorosilane, and 1.8% other components.

Example 1. 0.55 g of Copper (II) hydroxide was added to 50 g of the pre-fractionation product obtained in Comparative Example 1 and this system was heated and agitated for 3 hours at 130° C. in a nitrogen atmosphere. When this reaction mixture was analyzed by capillary GLC and $^{13}$C-nuclear magnetic resonance analysis, it was found that 98.9% of the abovementioned 1-methyl-2methacryloxyethyldimethylchlorosilane had been decomposed. Next, 0.03 g of 2,3-di-t-butyl-4-methylphenol was added to this reaction mixture, and the reaction mixture was distilled under reduced pressure at 5 mmHg producing a fraction with a boiling point of 92° to 105° C. This fraction was subjected to $^{13}$C-nuclear magnetic resonance analysis and $^{29}$Si-nuclear magnetic resonance analysis; and it was ascertained that this fraction consisted of 98.8% 3-methacryloxypropyldimethylchlorosilane, 0.0% 1-methyl-2-methacryloxyethyldimethylchlorosilane, 0.3% 3-methacryloxypropyl(methacryloxy)dimethylsilane,0.0% methacryloxydimethylchlorosilane, 0.0% dimethyldichlorosilane,and 0.9% other components.

Comparative Example 2. The pre-fractionation product obtained in Comparative Example 1 was heated and agitated for 3 hours at 130° C. in a dry nitrogen atmosphere. When this product was analyzed by $^{13}$C-nuclear magnetic resonance there was no change in composition, and no decomposition of the abovementioned 1-methyl-2-methacryloxyethyldimethylchlorosilane had occurred.

Example 2. 1.01 g of Copper (II) acetate was added to 50 g of the pre-fractionation product obtained in Comparative Example 1, and this system was heated and agitated for 3 hours at 130° C. in a nitrogen atmosphere. When this reaction mixture was analyzed by capillary GLC and $^{13}$C-nuclear magnetic resonance analysis, it was found that 95.6% of the abovementioned 1-methyl-2-methacryloxyethyldimethylchlorosilane had been decomposed. Next, 0.03 g of 2,3di-t-butyl-4-methylphenol was added to this reaction mixture, and the reaction mixture was distilled under reduced pressure at 5 mmHg producing a fraction with a boiling point of 92° to 105° C. This fraction was subjected to $^{13}$C-nuclear magnetic resonance analysis and $^{29}$Si-nuclear magnetic resonance analysis and it was ascertained that this fraction consisted of 98.5% 3-methacryloxypropyldimethylchlorosilane,0.0% 1-methyl-2-methacryloxyethyldimethylchlorosilane, 0.4% 3-methacryloxypropyl(methacryloxy)dimethylsilane, 0.0% methacryloxydimethylchlorosilane, 0.0% dimethyldichlorosilane, and 1.1% other components.

Example 3. 0.44 g of Copper (II) oxide was added to 50 g of the pre-fractionation product obtained in Comparative Example 1, and this system was heated and agitated for 3 hours at 130° C. in a nitrogen atmosphere. When this reaction mixture was analyzed by capillary GLC and $^{13}$C-nuclear magnetic resonance analysis, it was found that 96.7% of the abovementioned 1-methyl-2-methacryloxyethyldimethylchlorosilane had been decomposed. Next, 0.03 g of 2,3di-t-butyl-4-methylphenol was added to this reaction mixture and the reaction mixture was distilled under reduced pressure at 5 mm Hg, thus producing a fraction with a boiling point of 92° to 105° C. This fraction was subjected to $^{13}$C-nuclear magnetic resonance analysis and $^{29}$Si-nuclear magnetic resonance analysis and it was ascertained that this fraction consisted of 98.7% 3-methacryloxypropyldimethylchlorosilane, 0.0% 1-methyl-2-methacryloxyethyldimethylchlorosilane, 0.3% 3-methacryloxypropyl(methacryloxy)dimethylsilane, 0.0% methacryloxydimethylchlorosilane, 0.0% dimethyldichlorosilane, and 1.0% other components.

Example 4. 0.89 g of Copper (II) sulfate was added to 50 g of the pre-fractionation product obtained in Comparative Example 1 and this system was heated and agitated for 3 hours at 130° C. in a nitrogen atmosphere. When this reaction mixture was analyzed by capillary GLC and $^{13}$C-nuclear magnetic resonance analysis, it was found that 66.3% of the abovementioned 1-methyl-2-methacryloxyethyldimethylchlorosilane had been decomposed. After this reaction mixture was heated and agitated for an additional 3 hours at 130° C., it was found that 97.0% of the abovementioned 1-methyl-2-methacryloxyethyldimethylchlorosilane had been decomposed. Next, 0.03 g of 2,3di-t-butyl-4-methylphenol was added to this reaction mixture, and the reaction mixture was distilled under reduced pressure at 5 mm Hg, thus producing a fraction with a boiling point of 92° to 105° C. This fraction was subjected to $^{13}$C-nuclear magnetic resonance analysis and $^{29}$Si-nuclear magnetic resonance analysis and it was ascertained that this fraction consisted of 98.0% 3-methacryloxypropyldimethylchlorosilane, 0.0% 1-methyl-2-methacryloxyethyldimethylchlorosilane, 0.4% 3-methacryloxypropyl(methacryloxy)dimethylsilane, 0.0% methacryloxydimethylchlorosilane, 0.0% dimethyldichlorosilane, and 1.6% other components.

Comparative Example 3. 1.0 g of Copper (II) oxide and 0.1 g of 2,6-di-t-butyl-4-methylphenol were added to 50 g of the pre-fractionation product obtained in Comparative Example 1, after which this mixture was distilled under reduced pressure at 5 mmHg and a fraction with a boiling point of 92° to 105° C. was collected. This fraction was subjected to $^{13}$C-nuclear magnetic resonance analysis and $^{29}$Si-nuclear magnetic resonance analysis and it was ascertained that this fraction consisted of 96.1% 3-methacryloxypropyldimethylchlorosilane, 1.4% 1-methyl-2-methacryloxyethyldimethylchlorosilane, 0.8% 3-methacryloxypropyl(methacryloxy) dimethylsilane, 0.2% methacryloxydimethylchlorosilane, 0.2% dimethyldichlorosilane, and 1.3% other components.

I claim:

1. A method for purifying 3-methacryloxypropyldimethylhalosilanes comprising contacting a mixture comprising 3-methacryloxypropyldimethylhalosilane and 1-methyl-2-methacryloxyethyldimethylhalosilane with a copper compound selected from the group consisting of copper hydroxides, copper salts other than copper halides, and copper oxides thereby effecting decomposition of the 1-methyl-2-methacryloxyethyldimethylhalosilane to a compound separable from the 3-methacryloxypropyldimethylhalosilane by fractional distillation.

2. A method according to claim 1, where the copper compound is selected from the group consisting of copper(I) hydroxide, copper(II) hydroxide, copper(I) sulfate, copper (II) sulfate, copper(I) nitrate, copper(II) nitrate, copper(I) acetate, copper(II) acetate, copper(I) oxide, and copper(II) oxide.

3. A method according to claim 1, where the copper compound is selected from the group consisting of copper(I) acetate, copper(II) acetate, copper(I) sulfate, and copper(II) sulfate.

4. A method according to claim 1, where the copper compound is selected from the group consisting of copper (II) sulfate and copper(II) acetate.

5. A method according to claim 1, where the amount of the copper compound is in a range of 0.01 to 20 parts by weight based on the weight of the 3-methacryloxypropyldimethylhalosilane.

6. A method according to claim 1, where the amount of the copper compound is in a range of 0.1 to 10 parts by weight based on the weight of the 3-methylacryloxypropyldimethylhalosilane.

7. A method according to claim 1, where the contacting of the mixture with the copper compound is effect at a temperature of 50° to 200° C.

8. A method for purifying 3-methylacryloxypropylmethyldihalosilanes comprising contacting a mixture comprising 3-methylacryloxypropylmethyldihalosilanes and 1-methyl-2-methacryloxyethylmethyldihalosilanes with a copper compound selected from the group consisting of copper hydroxides, copper salts other than copper halides, and copper oxides thereby effecting decomposition of the 1-methyl-2-methacryloxyethylmethyldihalosilane to a compound separable from the 3-methylacryloxypropylmethyldihalosilane by fractional distillation.

9. A method according to claim 8, where the copper compound is selected from the group consisting of copper(I) hydroxide, copper(II) hydroxide, copper(I) sulfate, copper (II) sulfate, copper(I) nitrate, copper(II) nitrate, copper(I) acetate, copper(II) acetate, copper(I) oxide, and copper(II) oxide.

10. A method according to claim 8, where the copper compound is selected from the group consisting of copper(I) acetate, copper(II) acetate, copper(I) sulfate, and copper(II) sulfate.

11. A method according to claim 8, where the copper compound is selected from the group consisting of copper (II) sulfate and copper(II) acetate.

12. A method according to claim 8, where the amount of the copper compound is in a range of 0.01 to 20 parts by weight based on the weight of the 3-methylacryloxypropylmethyldihalosilane.

13. A method according to claim 8, where the amount of the copper compound is in a range of 0.1 to 10 parts by weight based on the weight of the 3-methylacryloxypropylmethyldihalosilane.

14. A method according to claim 1, where the contacting of the mixture with the copper compound is effect at a temperature of 50° to 200° C.

* * * * *